United States Patent [19]
Brünker et al.

[11] Patent Number: 5,908,764
[45] Date of Patent: Jun. 1, 1999

[54] METHODS AND COMPOSITIONS FOR INCREASING PRODUCTION OF ERYTHROMYCIN

[75] Inventors: Peter Brünker; Wolfgang Minas, both of Zürich; Pauli Kallio, Friedlisberg; James E. Bailey, Zürich, all of Switzerland

[73] Assignee: Solidago AG, Hallwylstrasse, Switzerland

[21] Appl. No.: 08/861,450

[22] Filed: May 22, 1997

[51] Int. Cl.⁶ ..................................................... C12P 19/62
[52] U.S. Cl. ........................ 435/76; 435/172.3; 435/252.3
[58] Field of Search .................... 435/76, 172.3, 435/252.3

[56] References Cited

U.S. PATENT DOCUMENTS 5,049,493  9/1991  Khosla et al. ............................ 435/69.1
5,190,871  3/1993  Cox et al. ............................... 435/172.3

OTHER PUBLICATIONS

Emler et al., 1995, "Crystal structure of the flavohemoglobin from *Alcaligenes eutrophus* at 1.75 Å resolution," *The EMBO Journal* 14(24):6067–6077.
Tarricone et al., 1997, "Unusual structure of the oxygen-–binding site in the dimeric bacterial hemoglobin from Vitreoscilla sp.," *Structure* 5 (4):497–507.
Altenbuchner et al., 1992, *Meth. Enzymol.* 216:457–466.
Bevitt et al., 1992, *Eur. J. Biochem.* 204:39–49.
Bibb et al., 1986, *Fifth International Symposium on the Genetics of Industrial Microorganisms, Zagreb*, pp. 309–318.
Bierman et al., 1992, *Gene* 116:43–49.
Brünker et al., 1996, *Mol. Gen. Genet.* 251:307–315.
Clark et al., 1995, *Microbiology* 141:663–669.
Cortes et al., 1991, *Nature* 346:176–178.
Cramm et al., 1994, *J. Biol. Chem.* 269:7349–7354.
DeModena, J.A. et al., 1993, *Bio/Technology* 11:926–929.
Donadio and Hutchinson, 1991, *Gene* 100:231–235.
Donadio et al., 1991, *Science* 252:675–679.
Donadio et al., 1990, *J. Bacteriol.* 172:350–360.
Donadio et al., 1992, *Gene* 111:51–60.
Hanel et al., 1993, *Biotech. Lett.* 15:105–110.
Heydarian et al., 1996, *Biotechnol. Letts.* 18:1181–1186.
Hopwood et al., 1983, *J. Gen. Microbiol.* 129:2257–2269.
Horan et al., 1993, Abstract, *Joint Mtg of Soc. for Industr. Microbiol. and Canad. Soc. of Microbiol.*, Jul. 31–Aug. 6, 1996, Toronto, Canada.
Kallio et al., 1994, *Eur. J. Biochem.* 219:201–208.
Kallio et al., 1996, *Biotechnol. Prog.* 12:31–39.
Kallio et al., 1996, *Biotechnol. Prog.* 12:751–757:.
Kao et al., 1994, *Science* 265:509–512.
Khosla and Zawada, 1996, *Trends Biotechnol.* 14:335–41.
Khosla and Bailey, 1988, *Mol. Gen. Genet.* 214:158–161.
Kieser and Hopwood, 1991, *Meth. Enzymol.* 204:430–458.
Kuhstoss et al., 1991, *J. Mol. Biol.* 222:897–908.
Lal et al., 1996, *Crit. Rev. Microbiol.* 22(4):201–255.
Magnolo, S.K. et al., 1991, *Bio/Technology* 9:473–476.
Martin et al., 1975, *Tetrahedron* 31:1985–1989.
Mazodier (1989), *J. Bacteriol.* 171:3583–3585.
McDaniel et al., 1995, *Nature* 375:533.
Motamedi et al., 1995, *Gene* 160:25–31.
Paulus et al., 1990, *J. Bacteriol.* 172:2541.
Rausch and Lehmann, 1991, *Nucl. Acids Res.* 19:5187–5189.
Smokvina et al., 1990, *Gene* 94:53–59.
Tsai et al., 1995, *Biotechnol. Bioeng* 47:347–354.
Tsai et al., 1996, *Biotechnol. Bioeng.* 49:151–160.
Tuan et al., 1990, *Gene* 90:21–29.
Wakabayashi et al., 1986, *Nature* 322:481–483.
Weber et al., 1985, *J. Bacteriol.* 164:425–433.
Weber et al., 1991, *Science* 252:114.
Zak et al., 1990, *Eur. J. Clin. Mircorbiol. Infect. Dis.* 9:462–465.

*Primary Examiner*—James Ketter
*Attorney, Agent, or Firm*—Pennie & Edmonds LLP

[57] ABSTRACT

Methods and compositions for increasing the production of erythromycins are provided. In particular, the invention relates to the engineering of erythromycin-producing organisms to express a heterologous oxygen-binding protein.

20 Claims, 8 Drawing Sheets

METHODS AND COMPOSITIONS FOR INCREASING PRODUCTION OF ERYTHROMYCIN

FIELD OF THE INVENTION

Methods and compositions for increasing the production of erythromycins are provided. In particular, the invention relates to the engineering of erythromycin-producing organisms to express a heterologous oxygen-binding protein.

BACKGROUND OF THE INVENTION

Erythromycin is a potent antibiotic with current annual production of some 2,200 tons. This clinically useful, broad-spectrum macrolide antibiotic is naturally produced by the actinomycetes *Saccharopolyspora erythraea*. In spite of extensive classical strain development efforts, classical mutagenesis and selection, volumetric yields of erythromycin in fermentation processes remain rather low at 8 to 9 g/l, as compared to 5–10 fold higher yields in the case of penicillins. Hence, production costs remain high.

Genetic engineering is one approach to overcome the limitations of classical strain improvement programs (see, for review, Lal et al., 1996, *Crit. Rev. Microbiol.* 22(4):201–255). Thus far, recombinant DNA techniques with erythromycin-producing strains of *S. erythraea* have been attempted on only a few strains. The approach generally used has been to identify and clone the genes encoding antibiotic biosynthetic proteins, so as to modify or amplify them.

For example, Hanel et al. attempted to achieve higher levels of erythromycin A production in *S. erythraea* by inserting into the chromosome an extra copy of eryC1, a gene presumably involved in directly regulating expression of erythromycin biosynthetic genes. Hanel et al., 1993, *Biotech. Lett.* 15:105–110. In the presence of thiostrepton, the selectable marker gene used for transformation, erythromycin A production of the transformants was two to three fold higher than the non-transformed strain. However, this increased production was lost in the absence of thiostrepton.

Other approaches that have been advanced to increase production levels of erythromycin have been to clone and amplify the biosynthetic erythromycin gene cluster (Lal et al. supra.), or to transfer the erythromycin biosynthetic gene cluster into another organism for potentially higher production. Kao et al., 1994, *Science* 265:509–512.

Production of some antibiotics is highly dependent on the amount of oxygen available during culture conditions. Clark et al., 1995, *Microbiology* 141:663–669. Accordingly, one way of increasing production of these types of antibiotics has been to engineer the microbial host to express the Vitreoscilla hemoglobin gene (VHb). Such a metabolic engineering strategy has been shown effective in increasing actinorhodin and cephalosporin C production in *Streptomyces coelicolor* and *Acremonium chrysogenum*, respectively (Magnolo, S. K. et al., 1991, *Bio/Technology* 9:473–476; DeModena, J. A. et al., 1993, *Bio/Technology* 11:926–929). At low dissolved oxygen levels (DO below 5% of air saturation), *S. coelicolor* transformed with the VHb gene produced ten fold more actinorhodin than non-transformed *S. coelicolor*. Magnolo et al., supra. However, when oxygen was not limiting (DO greater than 40% air saturation), both transformed and non-transformed strains produced similar amounts of antibiotic. Id. Production of cephalosporin C by the filamentous fungi *A. chrysogenum* is also severely reduced under low oxygen conditions. DeModena, J. A. et al., supra. Cultures of transformants expressing high levels of VHb yielded higher amounts of cephalosporin C, especially under oxygen limited conditions.

In contrast to these and many other antibiotics, erythromycin production does not appear sensitive to the levels of dissolved oxygen during culture. Heydarian et al., 1996, *Biotechnol. Letts.* 18:1181–1186; Clark et al., 1995, *Microbiol.* 141:663–669. Heydarian et al. reported that although growth of *S. erythraea* cultures is inhibited at a low constant dissolved oxygen tension (DOT) of 10% air saturation, the specific erythromycin production is virtually identical to that of a culture where the DOT did not fall below 65%. Similarly, Clark et al. found that erythromycin was produced in both oxygen limited and oxygen sufficient cultures. At the same time, however, Clark et al. discovered that a different actinomycete, *Amycolatopsis orientalis*, produced the antibiotic vancomycin only in oxygen-sufficient cultures. The results for both species were comparable in both shake flasks and bioreactors. Accordingly, availability of oxygen was not considered a critical limitation to erythromycin production, as long as the dissolved oxygen concentration in culture are above minimal levels required for growth.

SUMMARY OF THE INVENTION

The present invention is directed to methods and compositions for increased production of erythromycin. It has been discovered that the production of erythromycin by an erythromycin-producing organism is significantly increased when such organism also expresses a heterologous oxygen-binding protein.

In one aspect, the present invention provides an erythromycin-producing organism, wherein the organism also expresses a heterologous oxygen-binding protein.

Preferred oxygen-binding proteins for expression in erythromycin-producing organisms are those that bind oxygen reversibly such as globin proteins, and particularly Vitreoscilla hemoglobin and functional equivalents thereof.

Also encompassed by the instant invention are methods of increasing erythromycin production. In one aspect, the methods entail producing an erythromycin-producing organism that expresses a heterologous oxygen-binding protein. Methods of achieving the expression of oxygen-binding proteins in erythromycin-producing organisms include, but are not limited to, integrating a gene encoding the oxygen binding protein into the chromosome of the erythromycin-producing organism or transforming the organism to carry the gene extrachromasomally. In another aspect, the methods entail culturing an erythromycin-producing organism that expresses a heterologous oxygen-binding protein under conditions appropriate for production of erythromycin. The methods of the invention also encompass the collection of erythromycin produced from the cultured erythromycin-producing organism.

Finally, yet another aspect of the methods of the invention are novel methods of stably transforming *S. erythraea*.

BRIEF DESCRIPTION OF THE FIGURES

(FIG. 5A) and *S. erythraea*::vhb (FIG. 5B). The bars between FIGS. 5A and 5B indicate the duration of the respective feeds.

DETAILED DESCRIPTION OF THE INVENTION

Figure 1:
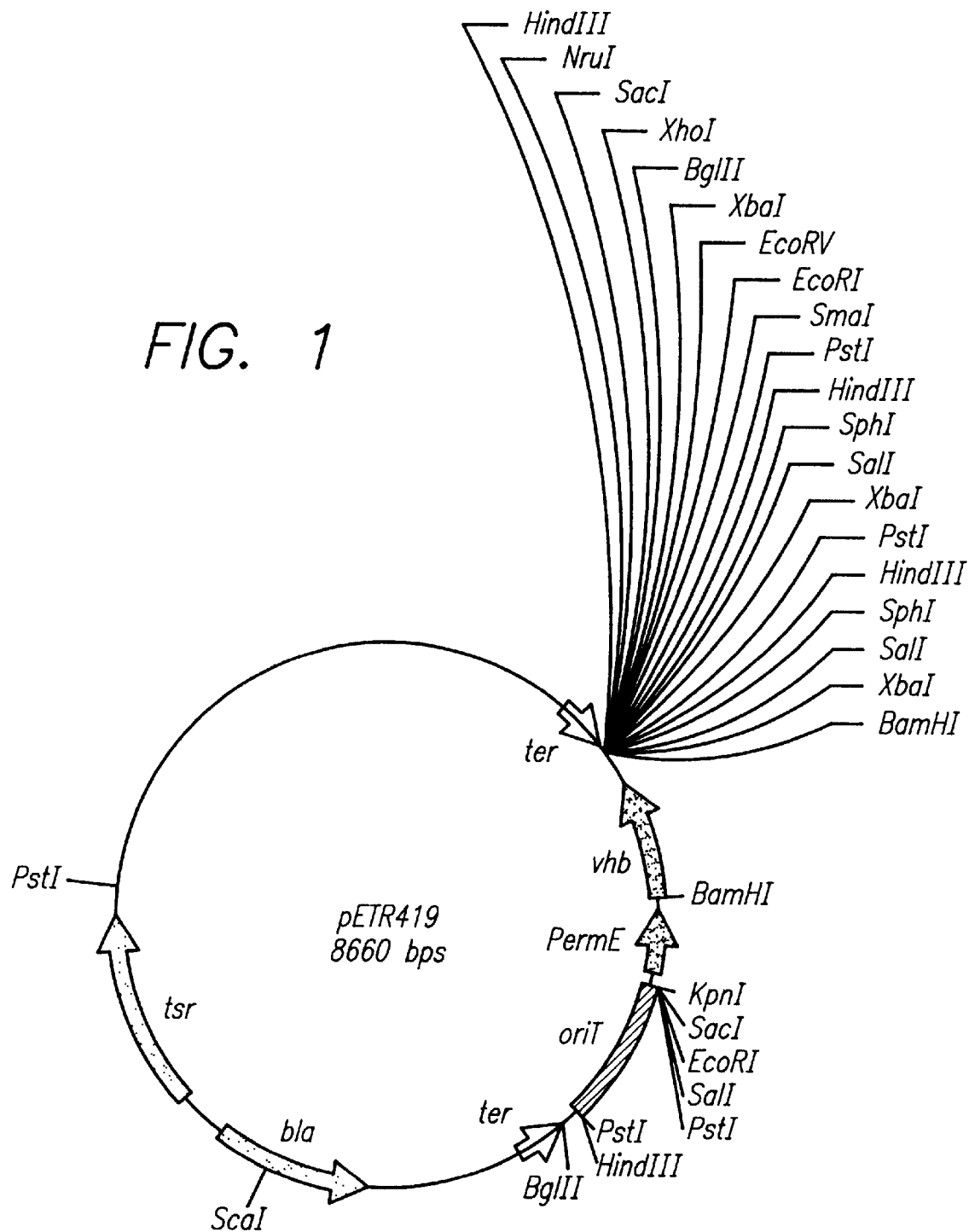
FIG. 1. is a diagram of plasmid pETR419, which was used for intergeneric conjugation between *E. coli* and *S. erythraea*.

A basis for the present invention is the unexpected discovery that erythromycin-producing organisms exhibit increased production of erythromycin when engineered to also express a heterologous oxygen-binding protein. In particular, a strain of *S. erythraea* stably transformed to express Vitreoscilla hemoglobin (VHb) produced up to 70% more erythromycin in bioreactor culture, as compared to the non-transformed parental strain.

As discussed more fully below in the Examples section, these surprising results appeared to be due to a direct effect of the heterologous VHb oxygen-binding protein on the erythromycin biosynthetic machinery. Therefore, the present invention is useful in any system for producing erythromycin that is known or can be used in the future.

Without intending to be limited to a particular mechanism, it is believed that the surprising results reported herein for production of erythromycin are due to either an increased level of intracellular oxygen, or an increased efficiency in intracellular oxygen utilization. Accordingly, the invention encompasses increasing the levels of oxygen-binding proteins within the cell of an erythromycin-producing organism, so as to increase the production of erythromycin.

Erythromycins and Erythromycin Production

An erythromycin-producing organism is any organism, known or to be discovered, that produces erythromycin, either naturally or through genetic engineering. Particularly preferred erythromycin-producing organisms are microorganisms such as bacteria and fungi. While any microorganism can be used as an erythromycin-producing organism, gram positive bacteria are particularly preferred, and especially actinomycetes. For most applications, it is important that the erythromycin-producing organism also express an erythromycin resistance gene.

For purposes of the instant invention, erythromycin includes the naturally occurring erythromycin A, erythromycin B, erythromycin C and erythromycin D. However, the preferred naturally occurring erythromycin is the active antibiotic erythromycin A. Also encompassed by the term erythromycin are active derivatives of erythromycin, which can be produced in vitro or through genetic engineering, such as erythromycin E, erythromycin F, 6-deoxyerythromycin B and 6-deoxyerythromycin A (see Weber et al., 1991, *Science* 252:114).

As noted above, erythromycin is naturally produced by *Saccharopolyspora erythraea*. These strains are commercially available from several different depositories (such as ATCC and NRRL), and can be selected through standard techniques well known in the field to obtain strains optimized for maximum production. For example, Paulus et al., 1990, *J. Bacteriol.* 172:2541, describes a TLC assay to assess erythromycin production. Naturally occurring variants that produce greater amounts of erythromycin can be subject to a high through-put mechanized screen as is commonly used in the pharmaceutical industry. See for example, Horan et al., 1993, Abstract, *Joint Mtg of Soc. for Industr. Microbiol. and Canad. Soc. of Microbiol.*, Jul. 31–Aug. 6, 1996, Toronto, Canada, and Zak et al., 1990, *Eur. J. Clin. Mircorbiol. Infect. Dis.* 9:462–465.

The entire erythromycin biosynthetic gene cluster has been cloned and sequenced. See Donadio et al., 1991, *Science* 262:675–679; Bevitt et al., 1992, *Eur. J. Biochem.* 204:39–49; and Cortes et al., 1991, *Nature* 346:176–178. The role of each domain in the erythromycin synthetic cluster has been proposed or deduced. Donadio et al., 1992, *Gene* 111:51–60. Erythromycin is comprised of a polyketide-derived 14 membered macrolactone ring, 6dEB, to which are attached two deoxysugars, cladinose and desoamine. Synthesis of 6dEB requires three adjacent eryA genes encoding large multifunctional polypeptides. Together, the three adjacent eryA genes comprise six modules of repeated motifs, each encoding a different synthetic unit specific for one of the elongation steps. Donadio et al., 1993, supra.

Efficient transformation systems and cloning vectors developed for manipulating *S. erythraea* are known and described in, for example, Donadio et al., 1990, *J. Bacteriol.* 171:350–360, Kieser and Hopwood, 1991, *Meth. Enzymol.* 204:430–458, and Donadio and Hutchinson, 1991, *Gene* 100:231–235. Accordingly, other engineered derivatives of *S. erythraea* useful for the production of erythromycin are those in which additional copies of all or part of the erythromycin gene cluster have been introduced into the cell, or those in which particular genes have been targeted and disrupted. Further, novel erythromycins can be produced through domain exchanges of the synthetic units of the erythromycin gene cluster, as described by Pieper et al., 1997, *Biochem.* 36:1846–1851; Luo et al., 1996, *Bioorg. Med. Chem.* 4:995–999; Bedford et al., 1996, *Chem. Biol.* 3:827–831; and oliynyk et al., 1996, *Chem. Biol.* 3:833–839. See for review Khosla and Zawada, 1996, *Trends Biotechnol.* 14:335–41; and McDaniel et al., 1995, *Nature* 375:533.

For example, Hanel et al., supra was able to increase erythromycin production by inserting into the chromosome an extra copy of the eryC1 gene. Weber et al., supra used targeted gene disruption of the eryF gene to obtain an *S. erythraea* strain that produced 6-deoxyerythromycin A, an acid derivative of erythromycin A. Similarly, Donadio et al., 1993, *PNAS:USA* 90, 7119 produced an erythromycin analog by reprogramming erythromycin synthesis.

Additionally, with the cloning and characterization of the erythromycin production gene cluster, other organisms may be engineered to produce erythromycin. Indeed, methods have been developed to clone the erythromycin biosynthetic genes into *E. coli* using an actinomycete/*E. coli* cosmid. Tuan et al., 1990, *Gene* 111:21. Further, Kao et al., 1994, *Science* 265:509–512, reported expression of the entire 6-deoxyerythronolide B synthase complex in *Streptomyces coelicolor*. Any engineered erythromycin-producing organisms, including but not limited to these examples, are within the scope of the invention.

Erythromycin may be collected from the cultured erythromycin-producing organism using methods well known to those of skill in the fermentation and pharmaceutical fields.

Expression Of Heterologous Oxygen-Binding Proteins In Erythromycin-Producing Organisms Heterologous expression of oxygen-binding proteins in erythromycin-producing organisms may be achieved by a variety of techniques known in the art. For purposes of the invention, the term "heterologous" is defined as expression of a protein that does naturally exist in that organism, or expression of a protein in a cellular location where it does not naturally occur, or an engineered increase in endogenous expression of a protein.

Oxygen-binding proteins expression in an erythromycin-producing organism may advantageously be achieved by recombinant DNA technology using techniques well known in the art. Such methods can be used to construct expression vectors containing a chosen oxygen-binding protein nucleotide sequence and appropriate transcriptional and translational control signals. These methods include, for example, in vitro recombinant DNA techniques, synthetic techniques, and in vivo genetic recombination. See, for example, the techniques described in Sambrook et al., 1989, infra, and Ausubel et al., 1989, infra. Alternatively, RNA capable of encoding oxygen-binding protein nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

The particular expression vector systems utilized to express nucleotide sequences encoding oxygen-binding proteins will depend upon the erythromycin-producing organism. Generally, the expression vector will comprise a promoter operably linked to nucleotide sequences encoding an oxygen binding protein and containing a transcriptional initiation sequence, and a transcriptional terminator. The promoter should be one that is transcriptionally active in the erythromycin-producing organism, and may be inducible or constitutive. The oxygen-binding protein encoded by the expression vector may be one that naturally occurs in the erythromycin-producing host, or may be from a different organism.

The expression construct should also encode appropriate recognition sequences for translational initiation in the erythromycin-producing organism. Optionally, the expression construct may contain signals for intracellular targeting of the oxygen-binding protein. For example, an oxygen-binding protein normally localized to the mitochondria, or the chloroplast, may instead be expressed in the cytoplasm by modifying the targeting signals on the translational product that are known to those of skill in the art. Finally, the vector may be designed for extrachromosomal maintenance, or for recombination into the chromosome.

Appropriate promoter sequences, transcriptional and translational initiation sequences, and terminators for a given host chosen as an erythromycin-producing organism are well known. Expression vectors for various hosts, such as plants, mammalian cells, insect cells, *E. coli*, Bacillus, and fungi (including Saccharomyces, Aspergillus, and Penicillium) are well known to those of ordinary skill in the art (see for a general review regarding expression in antibiotic-producing organisms, Lal et al., supra). Further, illustrated below by way of working examples are additional expression vectors appropriate for expression in actinomycetes, particularly Saccharopolyspora and Streptomycetes.

Alternatively, heterologous expression of an oxygen-binding protein may be achieved by altering expression of an oxygen-binding protein endogenous to the cell. As an example, homologous recombination may be used to replace an endogenous promoter with another more transcriptionally active promoter. Transcription may also be transactivated by inserting a transcritional enhancer adjacent the endogenous gene encoding an oxygen-binding protein, or by increasing the activity of transcriptional enhancers.

Oxygen-Binding Proteins For Use In The Invention

Oxygen-binding proteins useful for expression in erythromycin-producing organisms include any proteins which bind oxygen, particularly those which bind oxygen reversibly such as the globins. Preferred oxygen-binding proteins are those which are capable of increasing erythromycin production in erythromycin-producing organisms.

Oxygen-binding proteins that may be used in the invention include, but are not limited to, Vitreoscilla hemoglobin (VHb), *Alcaligenes eutrophus flavohemoprotein*, horse heart myoglobin, *E. coli* hemoprotein, *B. subtilis* hemoprotein, yeast flavohemoglobin, soybean leghemoglobin, lupin leghemoglobin, and sperm whale myoglobin. As noted above, the oxygen-binding protein may also be one that is endogenous to the erythromycin-producing organism.

The genes encoding a large number of oxygen-binding proteins have been cloned and their sequence determined. For example, known polynucleotide sequences of globin proteins useful in the instant invention include but are not limited to those encoding a cyanobacterium myoglobin (Potts et al., 1992, *Science* 256:1690–1692), *Scapharca inaequivalvis* hemoglobin (Gambacurta et al., 1993, *FEBS Lett.* 330:90–94), *Aplysia limacina* myoglobin (Cutruzzola et al., 1996, *Biochem. J.* 314:83–90), Ascaris hemoglobin (Sherman et al., 1992, *Proc. Natl. Acad. Sci. USA* 89:11696–11700), *Pseudoterranova decipiens* nemotode hemoglobin (Dixon et al., 1991, *Natl. Acad. Sci. USA* 88:5655–5659, and Dixon et al., 1992, *J. Mol. Evol.* 35:131–136), *Paramecium caudatum* hemoglobin (Yamauchi et al., 1992, *Biochem. Biophys. Res. Commun.* 182:195–200), *Rhizobium meliloti* haemoprotein (David et al., 1988, *Cell* 54:671–683), and *Saccharomyces cerevisiae* (Shimada et al., 1989, *J. Biochem.* 105:417–422).

Particularly suitable for use in the present invention are those oxygen-binding proteins which have relatively high $k_{off}$ rates such as VHb ($k_{off}$ 5600 s$^{-1}$; Orii and Webster, 1986, *J. Biol. Chem.* 261:3544–3547) or relatively low oxygen affinity such as horse heart myoglobin ($K_D$ 0.79 $\mu$M; Wittenberg et al., 1985, in *Nitrogen fixation research progress*, H. J. Evand et al. Eds. Martinus Nijhoff Publishers, Dordrecht, p. 354). Therefore, particularly preferred oxygen binding proteins can be those proteins with a $k_{off}$ rate for oxygen of greater than 10 s$^{-1}$, or a $K_D$ less than 0.5 $\mu$M, although it will be understood that oxygen-binding proteins with rate constants outside of these parameters will also be useful. Other examples of preferred oxygen-binding proteins are globins such as hemoglobin, myoglobin, and leghemoglobins. The properties of many oxygen-binding proteins, including globins, are disclosed in the literature. Additionally, techniques for determining the oxygen-binding properties of a protein such as a globin are well known to one of skill in the art and can be performed without undue experimentation.

An especially advantageous oxygen-binding protein for use in the instant invention, as described herein by way of working example, is Vitreoscilla hemoglobin ("VHb"). The complete sequence of the VHb gene is described in U.S. Pat. No. 5,049,493, supra. Mutants of VHb which bind oxygen are also within the scope of the present invention.

Another particularly advantageous oxygen-binding protein for use in the invention is *Alcaligenes eutrophus* flavohemoprotein (AeFH). This hemoglobin molecule shares 51% homology with VHb, and is very useful for biotechnological applications such as described herein. The complete primary sequence of AeFH and the nucleotide sequence encoding the protein are described in Cramm et al., 1994, *J. Biol. Chem.* 269:7349–7354.

Also encompassed within the scope of the invention is any nucleotide sequence that (a) hybridizes to the complement of the nucleotide sequence of the VHb or AeFH genes under highly stringent conditions, i.e., hybridization to filter-bound DNA in 0.5M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product that binds oxygen; and (b) any nucleotide sequence that hybridizes to the complement of the nucleotide sequence of the VHb or AeFH genes under less stringent conditions, such as moderately stringent conditions, i.e., washing in 0.2× SSC/0.1% SDS at 42° C. (Ausubel et al., 1989, supra), yet still encodes a functionally equivalent gene product that bind oxygen. Functional equivalents of VHb and AeFH include naturally occurring hemoglobin genes present in other species, and mutant VHb or AeFH whether naturally occurring or engineered that retain at least some reversible oxygen binding function. Species from which genes encoding functional equivalents of VHb and AeFH include but are not limited to bacterial species, and, in particular, those bacterial species found in soil, dung, and other oxygen-accessible, but poorly aerated, environments.

The invention also encompasses degenerate variants of nucleotide sequences that encode the amino acid sequence of the VHb protein, VHb mutants, AeFH protein, AeFH mutants, and functional equivalents of VHb or AeFH encoded by nucleotide sequences which hybridize to the complement of the nucleotide sequence of the VHb gene or the AeFH gene, respectively. For example, the nucleotide sequence can be altered so as to optimize amino acid codon usage for expression in the chosen erythromycin-producing organism.

The following examples are provided to further illustrate, but not limit, the invention described above.

EXAMPLES

Example 1

Insertion of VHb expression vectors into *S. erythraea*

We used two different approaches to obtain expression of VHb protein in *S. erythraea*. In the first approach, an intergeneric conjugation plasmid was used for transfer of an expression plasmid from *E. coli* to *S. erythraea*. The second approach, designed to increase stability of the expression construct, used a vector for chromosomal integration of a VHb expression construct.

Material and Methods

*S. erythraea*:spp is an industrial strain obtained from SOLIDAGO. *Streptomyces lividans* TK64 is described in Hopwood et al., 1983, *J. Gen. Microbiol.* 129:2257–2269. *E. coli* strains were grown at 37° C. in either dYT or LB liquid medium (Sambrook et al., 1989, "Molecular Cloning: A Laboratory Manual" Second Ed., Cold Spring Harbor Lab. Press.) or on dYT plates containing 1.6% agar. *S. erythraea* strains were maintained on R5 plates (Hopwood et al., 1985, "Genetic Manipulation of Streptomyces: A Laboratory Manual", John Innes Foundation, Norwich, U.K.) or incubated in SM liquid medium (Birr et al., 1989, *Appl. Microbiol. Biotechnol.* 30:358–363) at 34° C. *S. lividans* was maintained in the same media incubated at 30° C. Mycelial stocks of *S. erythraea* were kept at −80° C. in 30% glycerol, whereas *S. lividans* stocks were stored as spore solutions in 20% glycerol at −20° C. Media was supplemented with the appropriate antibiotics (100 µg/ml ampicillin, 12.5 µg/ml thiostrepton, 50 µg/ml kanamycin, 30 µg/ml chloramphenicol and 40 µg/ml nalidixic acid) when needed.

Mini-preparations of plasmid DNA were done by an alkaline lysis method described by Lee and Rasheed, 1990, *Biotechniques* 9:976–971. Genomic DNA from *S. erythraea* and *S. lividans* was isolated according to protocols by Hopwood et al., 1985, supra. Restriction enzymes, T4 DNA ligase, alkaline phosphatase, Klenow polymerase and polymerase were obtained from commercial sources and used as recommended by the manufacturers. Standard DNA techniques and Southern blot analysis were done as described by Sambrook et al., supra.

Polymerase chain reaction (PCR) for amplification of PmerR and VHb were performed with a GeneAmp 9600 PCR system (Perkin Elmer) using template specific conditions. All PCR fragments used for subsequent expression of VHb were confirmed by DNA sequencing with the dideoxy nucleotide chain termination method.

Competent *E. coli* XL1 Blue (Stratagene) and ET12567 (MacNeil et al., 1992) were prepared and transformed by the method of McKenney et al., 1981.

Preparation of *S. erythraea* protoplasts and PEG mediated transformation was performed according to a protocol of Hopwood et al., supra for *Streptomyces lividans*, with slight modifications. The cells were grown 4–5 days in TSB (Oxoid) containing 0.25% glycine. For protoplast formation, the final concentration of lysozyme was 8 mg/ml (instead of 4 mg/ml for *S. lividans*). Additionally, PEG3350 (Sigma) was used instead of PEG 1000 in the transformation reaction. For transformation of *S. erythraea*, non-methylated DNA isolated from *E. coli* ET12567 was used. Since regeneration of *S. erythraea* protoplasts seemed to be much slower compared to that of *S. lividans* protoplasts, the antibiotic overlay was done 48 hours after transformation.

Conjugational transfer of plasmids from *E. coli* to *S. erythraea* was performed on plates as described by Bierman et al., 1992, Gene 116:43–49.

To detect VHb protein, strains of *S. erythraea* were grown in 200 ml of SM medium for 4–5 days at 34° C. Cells were harvested, washed twice in buffer (100 mM Tris-HCl pH 7.5, 50 mM NaCl, 1 mM EDTA), resuspended in 20 ml of buffer and disrupted by passing 3× through a French press (Aminco SLM Instruments Inc.) operated at 1000–1500 psi. The soluble cellular fraction was used for Western blots (Winston et al., 1987) and for determination of the CO difference spectrum (Webster & Liu, 1974). Rabbit-anti-VHb serum was obtained from Cocalico Biologicals (Reanstown, Pa.). Protein concentration was determined by the method of Bradford (1976) using BIORAD dye reagent and bovine serum albumin as a standard.

Cultivation of *S. erythraea* was begun by inoculating 1.5 ml of a glycerol stock into a seed culture of 30 ml vegetative medium I (per liter: 16 g Argo corn starch, 10 g dextrin, 15 g soybean flour, 2.5 g NaCl, 5 ml corn steep liquor, 1 g $(NH_4)_2SO_4$, 6 ml soybean oil and 4 g $CaCO_3$, pH adjusted to 6.5) in a 250 ml baffled shake flasks. The seed culture was incubated for 40 h at 34° C. with 250 rpm agitation in a humidified rotary shake incubator (Infors). Three mls of this seed culture were then used to inoculate 27 ml of half strength fermentation medium I (per liter: 35 g corn starch, 32 g dextrin, 33 g soybean flour, 7 g NaCl, 20 ml corn steep liquor, 2 g $(NH_4)_2SO_4$, 6 ml soybean oil and 8 g $CaCO_3$ with the pH adjusted to 6.5). Cultivations for erythromycin production were run for 9 days with the following feeding procedure: soybean oil 0.2 ml/day from day 0–6; and n-propanol 0.1 ml/day from day 0–5 and 0.15 ml/day from day 6–9. Shake flasks were weighted daily and sterile water was added as necessary to compensate for evaporation.

A standard bioassay was applied to determine the erythromycin titers. Briefly, square 12 by 12 cm petri dishes were filled with 35 ml test medium (27.5 g/l TSB, 2 g/l glucose, 2% agar). After the medium had solidified, a lawn of *M. luteus* was prepared by pouring 35 ml of test media containing 35 μl of an *M. luteus* overnight culture in TSB onto the plates. After cooling, up to 6 sterile antibiotic test disks (Difco) were placed onto the plates. Ten μl samples were pipetted on the disks and plates were incubated for 2 days at 34° C. to allow a lawn of *M. luteus* to develop before the zone of growth inhibition was measured. Erythromycin titers were determined with erythromycin (Fluka) standards measured under the same conditions.

Results

Construction of a conjugable VHb expression plasmid

Intergeneric conjugation of plasmids from *E. coli* to *S. erythraea* has been described by Mazodier and coworkers (1989, *J. Bacteriol.* 171:3583–3585) and seemed in some cases even to be more efficient than transformation (Bierman et al., 1992, supra.). Thus, a VHb expression vector was constructed for conjugation into *S. erythraea*. An expression cassette consisting of the PermE* promoter (Bibb et al., 1985, *Gene* 38:E375–E368, and as cited in Motamedi et al., 1995, *Gene* 160:25–31), VHb (Khosla and Bailey, 1988, *Mol. Gen. Genet.* 214:158–161, and U.S. Pat. No. 5,049,493, issued Sep. 17, 1991, both of which are incorporated by reference herein) and the origin of transfer (oriT) from pPM927 (Smokvina et al., 1990, Gene 94:53–59) was constructed as shown in FIG. 1. This expression cassette was cloned into the Streptomyces/*E. coli* shuttle vector pJOE875 (Altenbuchner et al., 1992, *Meth. Enzymol.* 216:457–466) containing the Streptomyces origin of replication from plasmid pIJ350 (Hopwood et al., supra) and the pUC origin for replication in *E.coli*. The resulting plasmid was designated pETR419. After conjugation from *E. coli* S17.1 (genotype recA thi pro hsdR⁻M⁺ RP4:2-Tc:Mu:KmTn7 Tp$^R$ Sm$^R$; Simon et al., 1983, *Biotechnol.* 1:784–791) into *S. erythraea*, thiostrepton resistant exconjugants were selected. Counter-selection against *E. coli* was done with 40 μg/ml of nalidixic acid. The isolated *S. erythraea* exconjugants showed some VHb activity as judged by CO-binding assays. As confirmed by plasmid isolations from exconjugants, the expression plasmids tended to undergo recombination in *S. erythraea*.

Chromosomal integration of a VHb expression cassette in *S. erythraea* spp.

Plasmid instability prompted us to construct a vector for chromosomal integration of a VHb expression cassette in *S. erythraea*. To further avoid possible recombination in *S. erythraea* the PermE* promoter was replaced by another constitutive Streptomyces promoter. Previously it was shown that the two promoters of the mercury resistance determinant of *S. lividans* 1326 are constitutive in the absence of their negative regulator (MerR). Brünker et al., 1996, *Mol. Gen. Genet.* 251:307–315. Since *S. erythraea* was not expected to contain this mercury regulated repressor, the PmerR promoter was used for VHb expression. The complete sequence of the PmerR promoter has been reported in Sedlmeier and Altenbuchner, 1992, *Mol. Gen. Genet.* 236:76–85; Brunker et al., 1996, *Mol. Gen. Genet.* 251:307–315; and Klein et al., 1997, *Exs. (Switzerland)* 80:133–151.

PmerR and the VHb gene were amplified by PCR during which convenient restriction sites (SalI and EcoRI for PmerR; EcoRI and BamHI for VHb) were introduced at the end of the fragments and cloned into pIC19H (which only replicates in *E. coli*). The following primers were used to amplify the PmerR promoter:
forward: 5'TTGTCGACCCGCGGCGAATGCGCCGG (SEQ ID NO:1)
reverse: 5'TTGAATTCCCTTTCCACCAGCAGCTA (SEQ ID NO:2)

VHb sequence was amplified with appropriate restriction sites using the following primers:
forward: 5'TTGAATTCATGTTAGACCAGCAAACC (SEQ ID NO:3)
reverse: 5'GGATCCTTATTCAACCGCTTGAGC (SEQ ID NO:4)

Figure 2:
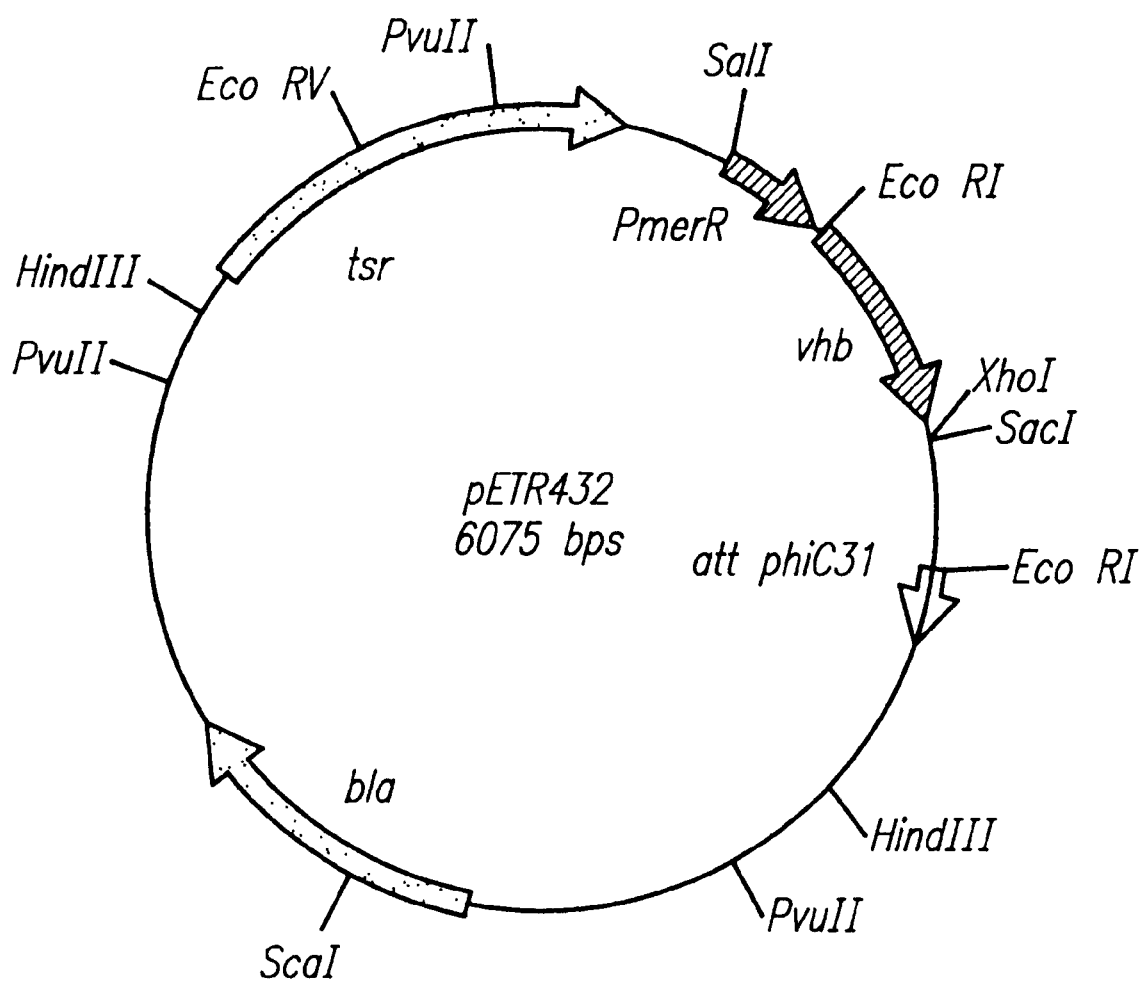
FIG. 2. is a diagram of plasmid pETR432 used for chromosomal integration of an expression construct comprising VHb under the control of the PmerR promoter.

In addition the thiostrepton resistance gene (tsr) (Hopwood et al., 1985, supra) for antibiotic selection in *S. erythraea* was inserted into this plasmid. The Streptomyces phage ɸC31 attachment site (att) was included in the expression vector to facilitate homologous recombination with the *S. erythraea* chromosome. The ɸC31 att sequence is described in Kuhstoss et al., 1991, *J. Mol. Biol.* 222:897–908 and Rausch and Lehmann, 1991, *Nucl. Acids Res.* 19:5187–5189, and can be found at GenBank accession: X60954. This construction was done under the assumption that *S. erythraea* also carries the ɸC31 att site. The resulting plasmid, pETR432 containing tsr, PmerR-vhb and att ɸC31 is shown in FIG. 2, and a diagram of its construction illustrated in FIG. 3. This plasmid was transformed using a modified transformation procedure into *S. lividans* TK64 and *S. erythraea*, as described above, resulting in strains *S. lividans*::vhb and *S. erythraea* ::vhb.

Expression and activity of VHb in transformants of both strains was confirmed by Southern and Western blot analysis and PCR (data not shown). In addition, a DNA fragment with VHb specific primers was amplified from chromosomal DNA of *S. erythraea*::vhb that was transformed with pETR432. The amplified fragment was cloned into pIC19H and sequenced to confirm the correct DNA sequence of VHb.

Biological activity of synthesized VHb was demonstrated by carbon monoxide (CO)-binding assays. A specific CO difference spectrum was observed in crude extracts of *S. lividans*::vhb and *S. erythraea*::vhb after treatment with CO while no peak at about 418 nm could be detected with the control strains that did not express VHb.

Stability of the recombinant *S. erythraea* strain

The genetic stability of the chromosomally integrated VHb expression cassette was determined by assaying retention of thiostrepton resistant in long term production cultures grown in the absence of thiostrepton. Cells of each sample taken for the erythromycin assays were plated onto R5 agar medium and replica plated on thiostrepton-containing agar plates. After 9 days of cultivation in the production medium without thiostrepton selection, the ratio of thiostrepton resistant to thiostrepton sensitive colonies was greater 97% (data not shown) demonstrating that the integrated VHb expression cassette in the chromosome of *S. erythraea* was stably maintained.

Discussion

Intergeneric conjugation of plasmids from *E. coli* into several Streptomyces strains is fairly efficient. In addition to *S. lividans* and *S. coelicolor, S. pristinaespiralis* and *S. viridochromogenes* can be used as recipients in such conjugation experiments (Mazodier et al., supra). Furthermore, it has been reported that plasmids could be conjugated from *E. coli* into *S. fradiae, S. ambofaciens* and even into *Sac. spinosa*. These latter strains are relatively resistant to transformation by PEG mediated protoplast transformation (Bierman et al., supra). All these conjugation systems require the origin of transfer (oriT) from RK2 in cis (Guiney & Yakobson, 1983, *PNAS:USA* 80:3595–3598), and transfer functions supplied in trans from the donor strain *E. coli* S17.1 (Mazodier et al., supra). Therefore a conjugable VHb expression plasmid, pETR419, was constructed as described above.

Plasmid pETR419 was transformed into *E. coli* S17.1 and then conjugated with *S. erythraea* to yield thiostrepton resistant exconjugants. Although the selected clones seemed to synthesize small amounts of active VHb, the expression plasmids were unstable in *S. erythraea*. This instability could result from homologous recombination between the PermE* fragment and the chromosomal ermE region within the erythromycin biosynthesis cluster of this strain.

Thus, it was decided to integrate a VHb expression cassette into the chromosome of *S. erythraea*. spp. and to replace PermE* by another constitutive promoter (PmerR) from *S. lividans* 1326. This heterologous promoter should reduce the chances for homologous recombination with the erythromycin biosynthetic genes. As the target for site specific integration, the Streptomyces phage φC31 attachment site was chosen which has previously been used for successful integration of plasmids into the chromosomes of *S. lividans, S. fradiae* and *S. ambofaciens* (Bierman et al., supra).

The resulting VHb expressing construct, pETR432, containing the PmerR-vhb expression cassette, the thiostrepton resistance gene (tsr) and a fragment carrying the φC31 attachment site was successfully transformed to *S. erythraea*. The presence of chromosomal integration of VHb was demonstrated by Southern blot analysis and amplification of VHb by PCR from chromosomal DNA of *S. erythraea*::vhb. All tested transformants showed the same restriction pattern in Southern blots which indicates that the plasmid integration occurred at a specific site, probably the φC31 attachment site of the *S. erythraea* chromosome. Integration at this site did not have any negative effect on the metabolism or viability of the recombinant strain. Furthermore, the integration was shown to be stable for at least 9 days in the absence of thiostrepton. Under these conditions, over 97% of the cells still retained the thiostrepton resistance phenotype.

CO-binding assays confirmed synthesis of active VHb. A typical VHb CO difference spectrum with an absorption maximum at 420 nm was observed in *S. lividans*. With crude extracts of *S. erythraea*::vhb, two absorption maxima were detected, one at 450 nm and one at 424 nm, respectively. While the peak at 424 nm is related to VHb expression the peak at 450 nm probably refers to a cytochrome P-450 monooxygenase (EryF) from *S. erythraea* (Katz and Donadio, 1995) as it is also found in *S. erythraea* without VHb. The absorption maximum at 424 nm shows synthesis of active VHb, although a slight shift in maximal absorption from 420 nm to 424 nm is observed.

From CO-binding assays it can be concluded that VHb activity in *S. lividans*::vhb is about 5-fold as high as in *S. erythraea*::vhb under the same conditions indicating that PmerR is more active in the strain from that it originally was isolated than in *S. erythraea* spp.

Example 2
Increased Production of Erythromycin

In this experiment, the effect of co-expression of an oxygen-binding protein, VHb, on erythromycin production in batch and bioreactor culture was investigated.

Materials and Methods

The bacterial strains used in this study were *S. erythraea* NRRL2338, and the erythromycin production strain *S. erythraea* ssp., and transformant *S. erythraea*::vhb described above in Example 1.

*S. erythraea* NRRL2338 was grown on R5 (Hopwood et al., 1985, supra) plates to obtain spores and to prepare spore suspensions for storage at −20° C. The production strain and its recombinant variant which do not sporulate were maintained either on R5 plates at 4° C. for up to 2 months or as mycelial cultures grown on V1 medium (see below), centrifuged and resuspended in 30% glycerol for storage at −70° C. in 1.5 ml aliquots. These stocks were used directly as inoculum for the different cultivations.

*Micrococcus luteus* (ATCC 9341) was used as challenge strain in the erythromycin bioassay.

Vegetative 1 (V1), Vegetative 2 (V2) and Fermentation (F1) medium were used for liquid cultures. Medium V1 contains per liter of reverse osmosis (RO) water 16 g Argo corn starch (CPC International Inc, Englewood Cliffs, N.J., U.S.A.), 10 g dextrin (D-2256, Sigma), 15 g soybean flour (32HO41, Sigma), 2.5 g NaCl (Merck), 5 ml corn steep liquor (C-Plus Cerestar F15855, about 50% solids, Cerestar France SA, Haubourdin), 1 g $(NH_4)SO_4$ (Roth), 6 m/l pure soybean oil (Nef Lebensmittel AG, Zurich, CH, catalog #01190) and 4 g $CaCO_3$ (Sigma). The pH was adjusted to 6.5. After autoclaving 20 minutes at 121° C. the medium should have a pH of about 7. One liter of V2 medium used for the second stage inoculum was made of 18 g corn starch, 12 g dextrin, 5 g soybean flour, 3 g NaCl, 6 ml corn steep liquor, 1.2 g $(NH_4)SO_4$, 6 ml soybean oil, and 5 g $CACO_3$, resuspended in RO water. After adjustment of the pH to 6.8 the medium was autoclaved 20 min at 121° C. The erythromycin production medium F1 contained, per liter of RO water, 35 g corn starch, 32 g dextrin, 33 g soybean flour, 7 g NaCl, 20 ml corn steep liquor, 2 g $(NH_4)SO_4$, 3 ml soybean oil, and 8 g $CACO_3$. After adjustment of the pH to 6.5 the medium was autoclaved 20 minutes at 121° C.

Sterile antifoam agent, Madzu DF 204 (PPG Ouvrie, Lesquin, France) was added prior to sterilization (about 0.5 ml/l) and during cultivations as needed. All media containing soybean flour started boiling at around 70° C. causing foaming problems when sterilized in bioreactors. Therefore, V2 medium was sterilized in the bioreactor without soybean flour which was autoclaved separately and added aseptically to the bioreactor. The original F1 medium was used at half strength only. All salts and dextrin were autoclaved separately and were added aseptically to the sterilized bioreactor containing all the other compounds. Due to the high portion of undissolved material, sterilization times for bioreactors were set to 50 min at 121° C. Test medium containing tryptic soy broth (TSB, Oxoid) supplemented with 2 g/l glucose and 1.5% agar was used for *M. luteus* based erythromycin bioassay.

Cultivations were performed in both shake flasks and bioreactors according to the following outline. For shake flask fermentations, 250 ml baffled Erlenmeyer flasks containing 30 ml culture were used. Flasks were incubated at 34° C. in an Infors RFI-150 incubator (Infors AG, Bottmingen, CH) with shaking at 250 rpm and a 2" stroke. Medium V1 was inoculated with 1.5 ml of a frozen stock culture and incubated with shaking. After 38 hrs, 3 mls of the seed culture was withdrawn to inoculate 27 mls of half strength F1 production medium. During the 9 day fermentation, the following compounds were fed once a day: soybean oil, 0.2 ml/day, was added from day 0 to day 6; and n-propanol was added at 0.1 ml/day from day 0 to day 5 and 0.15 ml/day from day 6 until the end of the fermentation. In addition, the flasks were weighed daily and sterile water was added to compensate for evaporation.

Bioreactor cultivations were performed in 3 stages. The first stage seed culture was grown in 35 ml V1 as described above for shake flask incubations. After 48 hours this culture was used to inoculate 3.5 liters of V2 medium. This second stage seed cultivation was done in an LH 210 5 liter bioreactor (Inceltech LH SGI S.A., France) equipped with a pitched blade turbine. The agitation speed was set to 800 rpm, air flow rate to 0.6 vvm, temperature was controlled at 34° C. and dissolved oxygen tension (DOT), pH and redox potential profiles were monitored. $CO_2$ and $O_2$ in the exhaust gas was monitored on-line with a VG Prima 600 mass spectrometer (VG Gas Analysis Systems, Middlewich, UK). After 40 hours, 1.5 liters of culture were transferred into an Infors ISF200 bioreactor (Infors AG, Bottmingen, CH) equipped with 2 Rushton turbines containing 10 liters of half strength F1 production medium. Cultivation conditions were as follows: temperature was set to 34° C., pH was controlled with $H_2SO_4$ to not exceed 7.2, agitation speed was set to 700 rpm and controlled by DOT signal to increase to 900 rpm if DOT was below 45% saturation, air flow rate for the first 12 hours was set to 0.37 vvm then changed to 0.83 vvm and falling to 0.7 vvm as feeding adds to the reactor volume, pressure was set to 0.1 bar. Continuous feeding of n-propanol, 2.4 ml/l/day from 12 to 160 hours, soybean oil, 4.8 ml/l/day from 25 hours until the end of the cultivation, and 15% dextrin, 48 ml/l/day from 30 to 90 hours, was realized with a Reglo-Digital MS4/8-100 four channel pump (Ismatec SA. Zurich, CH). Proper selection of tubing diameters compensated for the different flow rates. Low flow rates were achieved by the pump's discontinuous mode activating the pump once a minute to add the respective amounts of feed compounds. Redox potential, and $CO_2$ and $O_2$ concentrations in the exhaust gas, were monitored on-line as described above. In addition, free glucose was monitored hourly with a YSI 2700 Biochemistry Analyzer fitted with the 2730 Monitor and Control Module (YSI Inc., Yellow Springs, Ohio). Samples were drawn aseptically through a cross flow filter assembly (BioEngineering, Wald, CH) fitted with a 0.2 $\mu$m IRIS 6502 membrane (Phone-Poulenc Tech-Sep, Miribel, France). Daily samples of 50 or 100 ml were drawn for the determination of the erythromycin titer, CO binding studies and Western Blot analysis, and for microscopic inspection for mycelial morphology and possible contamination. Samples were stored at –20° C.

Erythromycin titers were determined as described above in Example 1.

CO-binding assay and Western blot analysis of the *S. erythraea* cultures were performed as described elsewhere (Kallio et al., 1996, *Biotechn. Prog.* 12:31–39; Sambrook et al., supra) with the following modifications. Following cell disruption using a French press (Aminco, SLM Instruments Inc., Urbana, Ill.) an ultracentrifugation step for 4 hours at 35,000 rpm in an SW4lTi rotor (Beckmann) was added in order to separate soy oil, soybean oil-bound small particles and cell debris from the cleared cell extract.

Results

Figure 4:
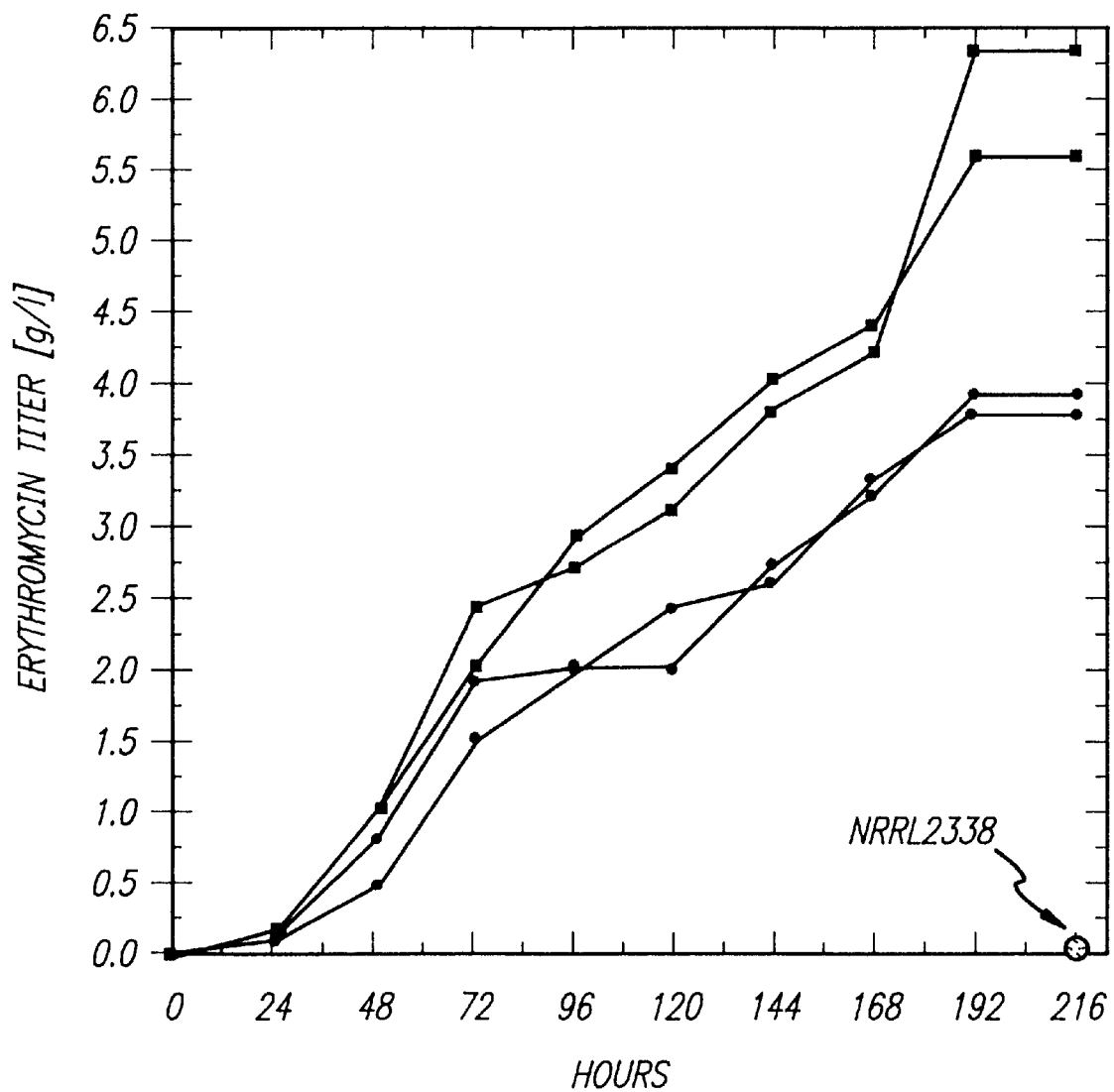
FIG. 4. summarizes the results of the shake-flask cultivations. Data points for the non-transformed *S. erythraea* spp. are circles. *S. erythraea*::vhb data points are represented by squares.

Erythromycin production in fed-batch shake flask cultivations was compared between the original production strain *S erythaea*::vhb and *S erythraea* NRRL2338. Experiments were conducted in 30 ml medium using baffled 250 ml shake flasks as described above. Samples were taken during the cultivation in production medium and analyzed for erythromycin titers. FIG. 4 summarizes the results of the shake-flask cultivations. The industrial strain produced 3.8–3.9 g/l under these conditions. This titer was confirmed in a second cultivation. The recombinant strain *S. erythraea*::vhb yielded between 5.6 and 6.3 g/l erythromycin. This represents a 45 to 63% increase in volumetric productivity. Furthermore, *S. erythaea*::vhb showed a more rapid onset of biosynthesis during the first three days and an additional jump in production between day 7 and 8 before reaching the final titer. These titers compared to 50 mg/l obtained with *S erythraea* NRRL2338 after 9 days and indicate a 100 fold increased erythromycin production in the highly developed industrial strains. Because of the genetic stability of *S. erythromycin*::vhb shake flask cultivations described above, thiostrepton was not used in any of the cultivations.

Bioreactor fed-batch cultivations were performed on a 10–15 liter scale. This scale is a useful representation of pilot production scale and permits withdrawal of the larger samples required to monitor VHb expression by Western blot analysis and VHb activity by CO-binding assays. As described above the second stage preculture was performed in a bioreactor. This cultivation method improved the reproducibility with which V2 cultivations could be performed. The pH and redox potential profiles for duplicate and triplicate cultivations were almost identical for the respective strains. During the first 16 hours of second stage cultivation, pH dropped to almost 6. After 16 hours, pH then increased sharply to above 8, reaching a maximum at around 24–26 hours after which pH fell again to values >7 at 40 hours. During production in half strength F1 medium, pH was controlled at less than 7.2.

Figure 5A:
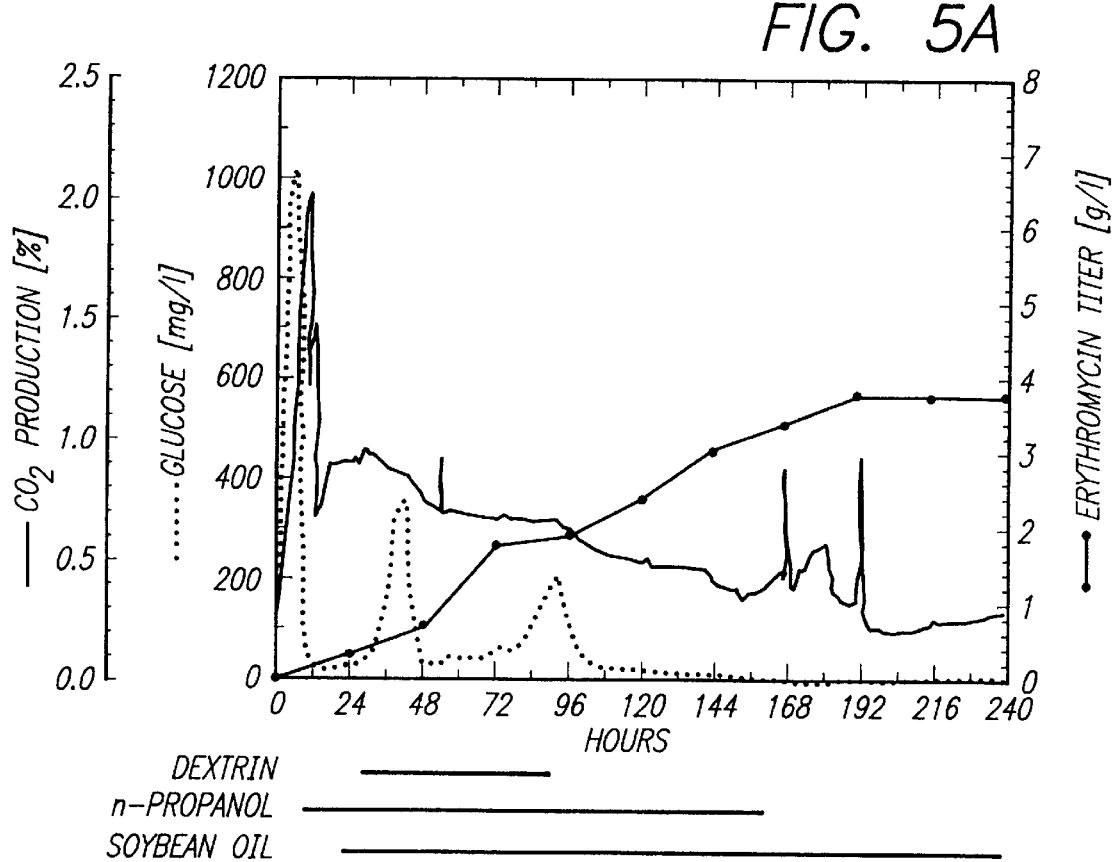
FIGS. 5A and 5B compare fermentation profiles from *S. erythraea* ssp.
Figure 5B:
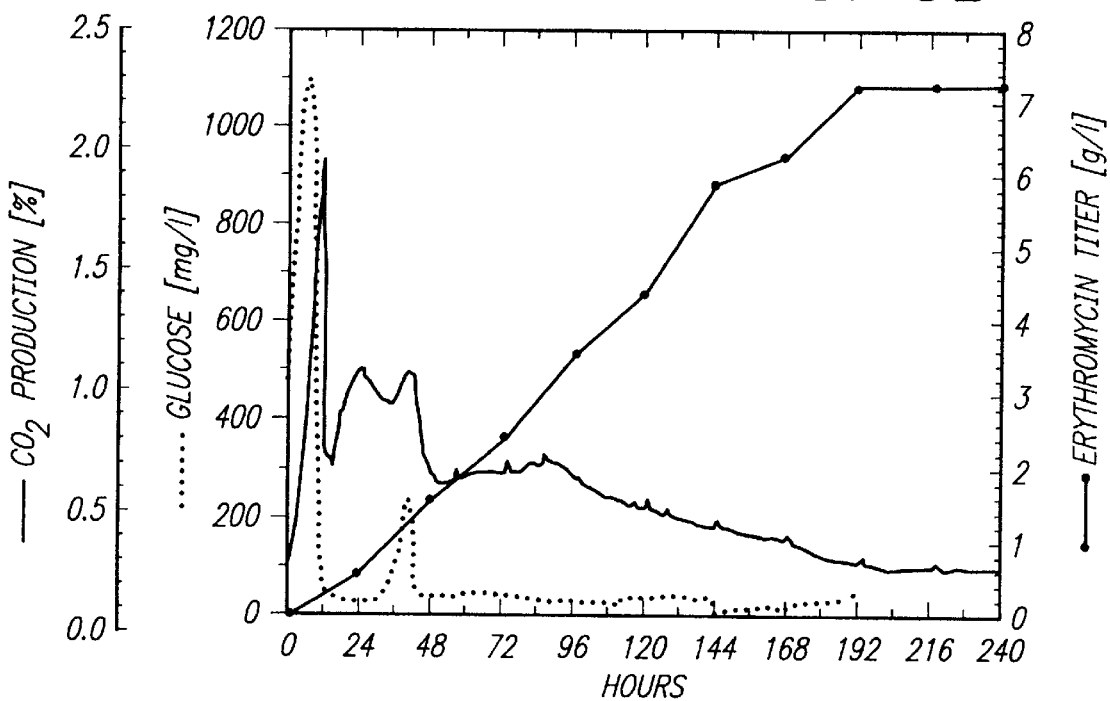

Fermentation profiles from *S erythraea* ssp. and *S. erythraea*::vhb are compared in FIG. 5. The bars on top indicate the duration of the respective feeds. It is interesting to note that with 3 exceptions no free glucose could be detected. The first and highest peak of free glucose, about 1 g/l, was measured during the first 12 hours after inoculation, the second peak after 38 hrs (following the start of the dextrin feed), and the third peak occurred at the end of the dextrin feed. Differences between the recombinant *S. erythraea*::vhb and the original *S. erythraea* ssp. were observed. These include the higher concentration of 0.4 g/l free glucose after 38 hours in the *S. erythraea* ssp. cultivation as compared to 0.25 g/l with the recombinant strain and the appearance of the third peak only with the original strain. These differences point to a slower growth of the original strain and a reduction of the growth rate after about 72 hours. This assumed reduction in growth rate coincided with a decrease in erythromycin production rate.

Figure 6:
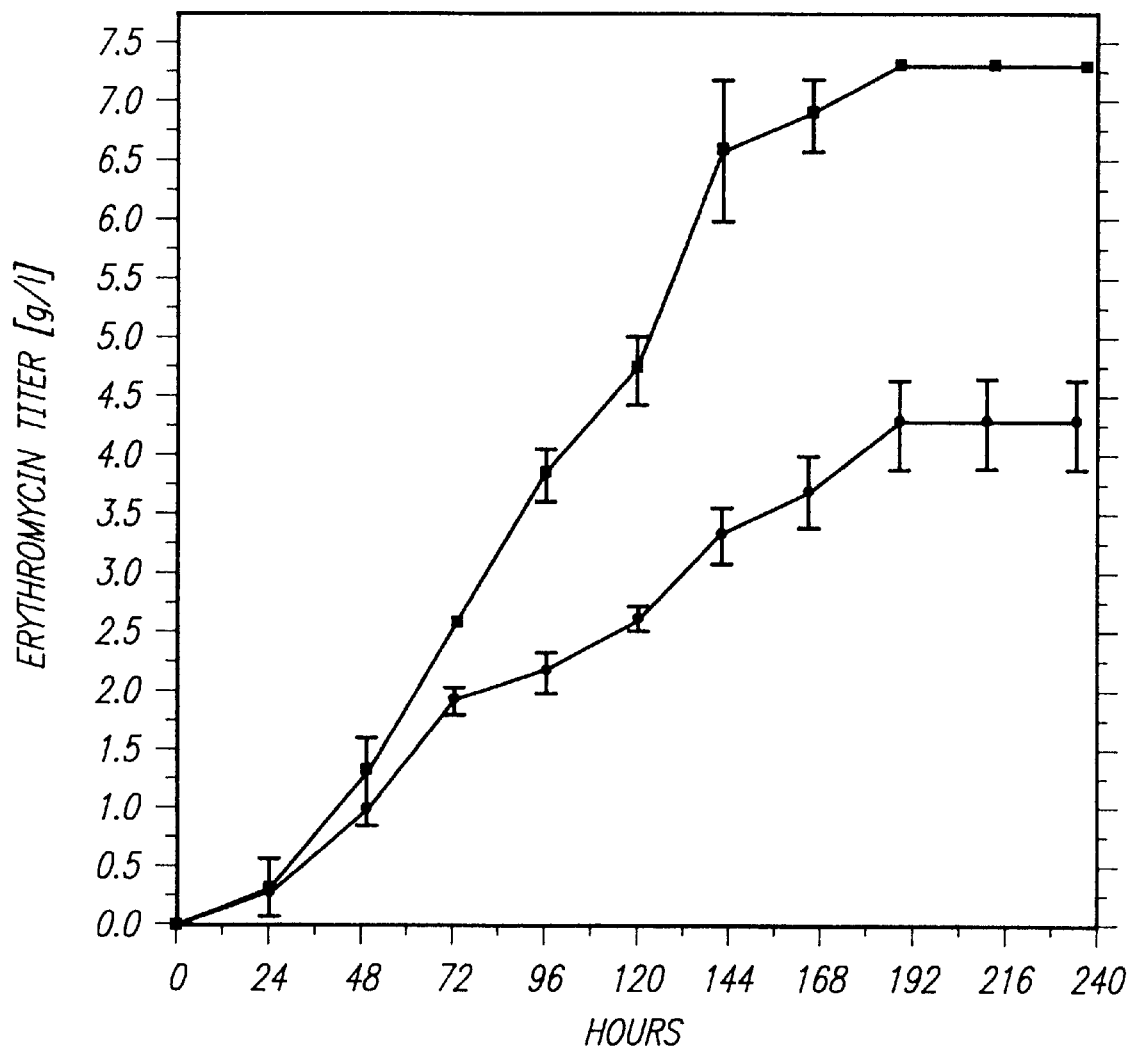
FIG. 6. summarizes the results of 5 bioreactor cultivations, three fermentations with *S. erythraea* ssp. (circles) and two cultivations with the recombinant *S. erythraea*::vhb (squares).

FIG. 6 summarizes the results of 5 such bioreactor cultivations, three fermentations with *S. erythraea* ssp. and two cultivations with the recombinant *S. erythraea*::vhb. Final erythromycin titers obtained were 7.25 g/l for the recombinant *S. erythraea* and 4.25 g/l for the original production strain. This corresponds to an increase in erythromycin production of about 70%. This increase in productivity was the result of a higher rate of erythromycin biosynthesis. The production rates were calculated for the time interval from 48 to 144 hours, and found to be 4.2 mg/h/l with the recombinant VHb expressing strain *S. erythraea*::vhb as compared to only 1.9 mg/h/l with the original production strain.

Microscopic analysis of the samples revealed that starting at about day 8 (192 hours) a progressive fragmentation of the mycelium could be observed. The disintegration of the mycelium was more pronounced in *S. erythraea* ssp. than in the recombinant *S. erythraea*::vhb.

Expression of the heterologous VHb protein in *S. erythraea*::vhb was analyzed to prove that this change in production is correlated with the expression of VHb in *S. erythraea*::vhb. Western blots were made with samples from cultivations with the recombinant and the original strain. A clear signal that corresponds to the positive control was detected in all samples from the *S. erythraea*::vhb throughout the cultivation. No VHb specific signal was detected in samples from cultivations with *S. erythraea* ssp. This result is additional proof that the recombinant strain is genetically stable and that the chromosomally integrated gene is transcribed throughout the erythromycin production phase.

The activity of the expressed gene was examined by CO binding studies. VHb is characterized by a well defined peak at 420 nm in CO binding assays. This VHb specific peak was detected in *S. erythraea*::vhb throughout the cultivation. No peak at 420 could be identified in the original *S. erythraea* ssp. The peak at 450 nm belongs to the cytochrome P-450 monoxygenase, eryF, of the erythromycin gene cluster which converts 6-deoxyerythonolide B to erythronolide B.

Discussion

The goal of this study was the development of an improved strain that would be genetically stable throughout the production process. We integrated only a single copy of our vector confirming the Vitreoscilla hemoglobin gene, a thiostrepton marker used for the initial isolation of transformants, and the phage φc31att site into the chromosome (Example 1, supra). Integration is expected to take place at the putative att site of the chromosome, a region that has no function in secondary metabolism. This is in contrast to the approach generally used in which modifications are made in the genes encoding for the biosynthesis or the regulation of biosynthesis of the antibiotics (Hanel et al., supra; Lal et al., supra).

Both shake flask and bioreactor cultivations at a scale of at least 10 liter proved that this genetically engineered *S. erythraea*::vhb was superior to the original strain. Bioreactor cultivations done as described above closely resemble an industrial process. *S. erythraea* ssp. was reported to produce between 5 to 7 g/l erythromycin under these conditions. In our hands the strain reproducibly produced around 4.5 g/l which is a little lower than the expected productivity. This is most likely due to modifications made to the original media formulation to substitute for certain complex compounds that were not available in Europe. Since we were primarily interested in comparing the original strain with its recombinant variant, we did not attempt to improve on our media or culture conditions.

Figures 1, 3:
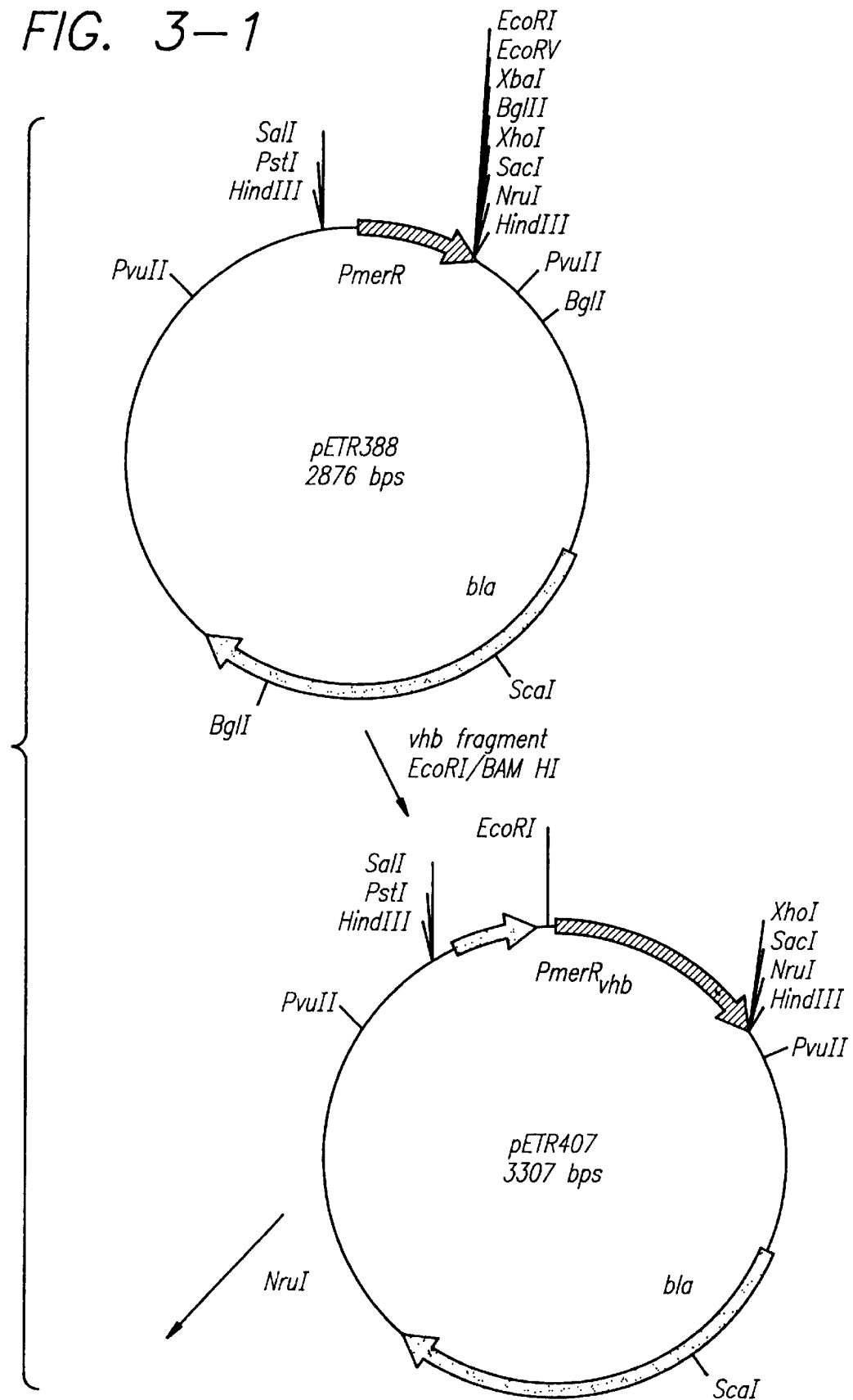
FIG. 3. illustrates the cloning steps performed to construct pETR432.
Figures 2, 3:
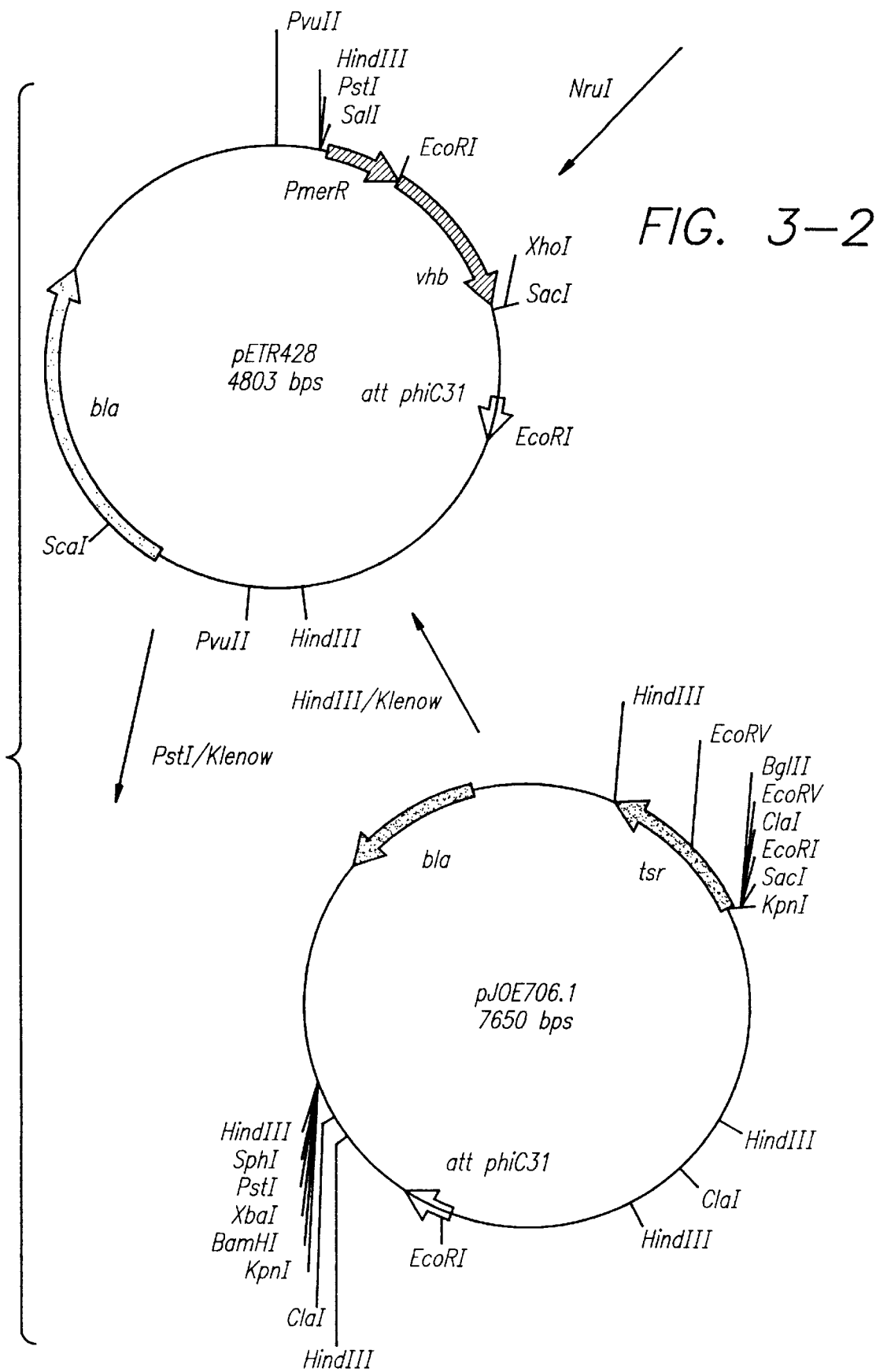
Figure 3:
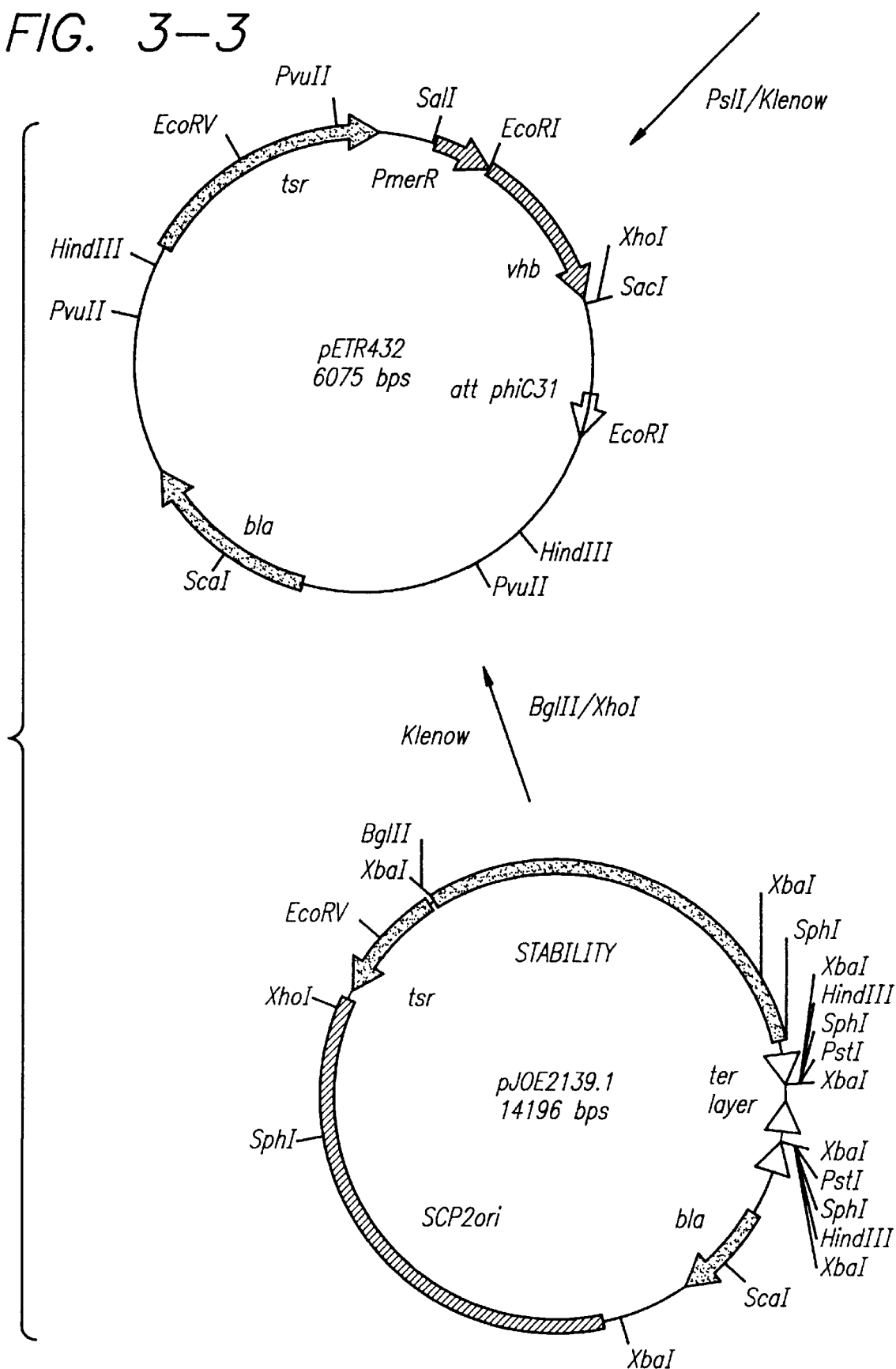

Comparing the volumetric yields of erythromycin for the two strains showed a 70% increased volumetric yield with the recombinant strain *S. erythraea*::vhb relative to the original strain. This significant difference could be attributed to a change in erythromycin biosynthesis rate. While after about 90 hours of cultivation the biosynthesis rate in *S. erythraea* ssp. dropped from initial high rate to a reduced rate of 1.9 ml/l/h, erythromycin production rate with *S. erythraea*:: vhb remained at the high rate of 4.2 mg/h/l (FIG. 3). It is not clear why this reduction in erythromycin production occurs with *S. erythraea* ssp. Interestingly, at about the same time, which is also the end of the dextrin feed, a transient accumulation of free glucose was observed in the cultivation with *S. erythraea* ssp. This points to a reduction in growth rate that could not be observed with the recombinant strain. The limitation that caused this apparent change in growth and erythromycin production rates remains unknown. All differences, however, should be the result of the genetic manipulation of the recombinant strain. Fortunately, *S. erythraea*::vhb was genetically stable and it was not required to supplement the medium for selection with thiostrepton, a substance that is known to cause pleiotropic effects. Thus, it can be argued that the increase in erythromycin productivity was due to the expression of the vhb gene. That the expressed VHb was functional throughout the cultivation was shown by Western blot analysis and CO-binding assays.

How VHb expression aids growth or antibiotic production is unknown. It is believed that VHb improves oxygen availability by increasing the intracellular oxygen concentration under microaerobic culture conditions (Kallio et al., 1994, *Eur. J. Biochem.* 219:201–208). Despite a high >45% DOT throughout the cultivations, oxygen might become limited in the mycelium aggregated in a viscous medium. Interactions of VHb and cytochrome o and cytochrome d in *E. coli* have been reported (Wakabayashi et al., 1986, *Nature* 322:481–483; Tsai et al., 1996, *Biotechnol. Bioena.* 49:151–160). The interaction with these terminal oxidases is argued to increase microbial respiration and growth. This apparent requirement for oxygen is in contrast to observations that specific erythromycin production remains unchanged at aerobic, 60% DOT, microaerobic, 10% DOT, or even anaerobic culture conditions (Heydarian et al., supra; Clark et al., supra).

Erythromycin biosynthesis involves the action of a cytochrome P450 monoxygenase, eryF1, which performs the C6-hydroxylation converting 6-deoxyerythronolide B to erythronolide B. This reaction step, taken in conjunction with the results presented herein, raises the possibility of a direct interaction between VHb and the monoxygenase of erythromycin biosynthesis. Regardless, the results demonstrate the usefulness of genetic engineering for the improvement of erythromycin production strains by providing a stable recombinant strain expressing the functional heterologous oxygen-binding VHb gene.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An erythromycin-producing organism, wherein the organism further expresses a heterologous oxygen-binding protein.

2. The organism of claim 1 which is *Saccharopolyspora erythraea*.

3. The organism of claim 1, wherein the oxygen-binding protein is a globin protein.

4. The organism of claim 3, wherein the globin protein is selected from the group consisting of Vitreoscilla hemoglobin, *Alcaligenes eutrophus* flavohemoprotein, horse heart myoglobin, *E. coli* hemoprotein, *B. subtilis* hemoprotein, yeast flavohemoglobin, soybean leghemoglobin, lupin leghemoglobin, and sperm whale myoglobin, or their functional equivalents.

5. The organism of claim 4 wherein the globin protein is Vitreoscilla hemoglobin.

6. The organism of claim 2 wherein the gene is integrated into the *Saccharopolyspora erythraea* chromosome.

7. The organism of claim 1, wherein the erythromycin is selected from the group consisting of erythromycin A, erythromycin B, erythromycin C, erythromycin D, erythromycin E, erythromycin F, and 6-deoxyerythromycin A.

8. A method of increasing erythromycin production, the method comprising:
   culturing an erythromycin-producing organism that expresses a heterologous gene encoding an oxygen-binding protein under conditions appropriate for production of erythromycin.

9. The method of claim 8 wherein the organism is *Saccharopolyspora erythraea*.

10. The method of claim 8, wherein the oxygen-binding protein is a globin protein.

11. The method of claim 9, wherein the globin protein is selected from the group consisting of Vitreoscilla hemoglobin, *Alcaligenes eutrophus* flavohemoprotein, horse heart myoglobin, *E. coli* hemoprotein, *B. subtilis* hemoprotein, yeast flavohemoglobin, soybean leghemoglobin, lupin leghemoglobin, and sperm whale myoglobin, or their functional equivalents.

12. The method of claim 11 wherein the globin protein is Vitreoscilla hemoglobin.

13. The method of claim 9 wherein the heterologous gene is integrated into a chromosome of the cell.

14. The method of claim 8 wherein the erythromycin is selected from the group consisting of erythromycin A, erythromycin B, erythromycin C, erythromycin D, erythromycin E, erythromycin F, and 6-deoxyerythromycin A.

15. A method of producing erythromycin, the method comprising:

collecting erythromycin from a culture of an erythromycin-producing organism that expresses a heterologous gene encoding an oxygen-binding protein.

16. A method of making an improved erythromycin-producing organism, the method comprising producing an erythromycin-producing organism that expresses a heterologous oxygen-binding protein.

17. The method of claim 16, wherein the method comprises transforming the erythromycin-producing organism with an expression construct that directs expression of the oxygen-binding protein in the erythromycin-producing organism.

18. The method of claim 17, wherein the expression construct is integrated into the chromosome of the erythromycin-producing organism.

19. The method of claim 17, wherein the expression construct is maintained on a plasmid in the erythromycin-producing organism.

20. The method of claim 16, wherein the organism is *Saccharopolyspora erythraea*.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:1:

TTGTCGACCC GCGGCGAATG CGCCGG                                              26

(2) INFORMATION FOR SEQ ID NO:2:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:2:

TTGAATTCCC TTTCCACCAG CAGCTA                                              26

(2) INFORMATION FOR SEQ ID NO:3:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:3:

TTGAATTCAT GTTAGACCAG CAAACC                                              26

(2) INFORMATION FOR SEQ ID NO:4:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:4:

GGATCCTTAT TCAACCGCTT GAGC                                                24